United States Patent [19]

Jagrovic

[11] 3,970,460
[45] July 20, 1976

[54] DIAZOTYPE COMPOSITION
[75] Inventor: Petar Jagrovic, Bern, Switzerland
[73] Assignee: Multitec AG, Switzerland
[22] Filed: Mar. 15, 1974
[21] Appl. No.: 451,556

[30] Foreign Application Priority Data
  Mar. 28, 1973 Switzerland.................... 4459/73

[52] U.S. Cl. ................. 96/91 R; 96/49;
          96/75; 260/141; 260/142
[51] Int. Cl.² ....................... G03C 1/54
[58] Field of Search .............. 96/91 R, 75, 49;
          260/141 R, 141, 142

[56] References Cited
UNITED STATES PATENTS

| | | | |
|---|---|---|---|
| 2,286,701 | 6/1942 | Werner | 96/91 R |
| 3,016,298 | 1/1962 | Sonders et al. | 96/91 R |
| 3,028,240 | 4/1962 | Werner et al. | 96/91 R |
| 3,311,475 | 3/1967 | Van Loon et al. | 96/91 R |
| 3,397,985 | 8/1968 | Hendrickx | 96/91 R |
| 3,407,066 | 10/1968 | Mustacchi et al. | 96/91 R |
| 3,442,652 | 5/1969 | Hectors et al. | 96/91 R |
| 3,459,550 | 8/1969 | Munder et al. | 96/91 R |
| 3,615,578 | 10/1971 | Hectors et al. | 96/91 R |
| 3,736,143 | 5/1973 | Frommeld et al. | 96/91 R |
| 3,775,131 | 11/1973 | Hendriks et al. | 96/91 R |

FOREIGN PATENTS OR APPLICATIONS

| 43-4927 | 2/1968 | Japan | 96/91 R |
|---|---|---|---|

OTHER PUBLICATIONS
Dinaburg, M. S., "Photosensitive Diazo Compounds," The Focal Press, 1964, pp. 74-75.
Kosar, J., "Light-Sensitive Systems," Wiley & Sons, 1965, p. 213.

Primary Examiner—Charles L. Bowers, Jr.
Attorney, Agent, or Firm—Stevens, Davis, Miller & Mosher

[57] ABSTRACT
A diazotype material is disclosed containing a novel 2-substituent-3-thio-5-alkoxybenzene diazonium compound of formula I

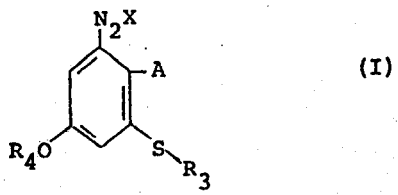

wherein
X is an anion,
A is the group

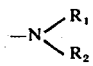

or $-OR_4$
in which
$R_1$ is hydrogen, an alkyl radical with 1-8 carbon atoms, a substituted phenyl, cycloalkyl, or aralkyl radical or a heterocyclic radical,
$R_2$ is an alkyl radical with 1-8 carbon atoms, a $-COOR_5$ group in which
$R_5$ signifies hydrogen, an alkyl radical with 1-8 carbon atoms, a cycloalkyl, aryl, aralkyl, or alkylaryl radical or a heterocyclic radical, or a group of

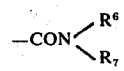

or $-SO_2R_6$
in which
$R_6$ and $R_7$ stand independently of one another for hydrogen or a hydroxy, alkoxy, alkyl with 1-4 carbon atoms, or phenyl radical,
$R_1$ and $R_2$ together with the nitrogen may be a morpholino, a methyl-substituted morpholino, pyrrolidino, or piperidino group,
$R_3$ is an alkyl radical with 1-8 carbon atoms, an aralkyl, alkoxyaryl, haloaryl, alkoxyalkyl, or cycloalkyl radical or a heterocyclic radical, and
$R_4$ is an alkyl, branched or unbranched lower alkyl, cycloalkyl, or aralkyl radical.

8 Claims, No Drawings

DIAZOTYPE COMPOSITION

The present invention relates to diazotype material containing novel diazonium compounds.

As is well known, a single-component diazotype material consists of a flat carrier, such as transparent or opaque paper, transparent or matted synthetic film, or aluminum sheeting, which is coated with a photosensitive layer. The layer contains one or more photosensitive diazonium salts and stabilizing additives such as tartaric acid, boric acid, citric acid, aluminum sulfate, or other acid salts.

The diazotype material is selectively exposed to light under a transparent pattern and then brought into contact with an aqueous, coupler-containing, buffered developing liquid. The image is produced in the unexposed parts of the diazotype material in that the non-decomposed diazonium compound is coupled with the coupler from the developer solution into a waterinsoluble azo dye. The developer solution contains one or more very actively reacting coupler components, such as phloroglucinol, resorcinol, acetonacetic anilide, etc., a buffer system which makes possible the retention of the desired pH, consisting of buffer salts such as ammonium salts, alkaline earth salts, or alkalimetal salts of acetic, citric, formic, adipic, maleic, phosphoric, boric, or carbonic acid, and either alkalis such as sodium, potassium, or lithium hydroxide if the developer is supposed to be alkaline adjusted, or acids such as tartaric, citric, or benzoic acid if the developer is supposed to be neutrally or weakly acid adjusted. As further additives, it contains a wetting agent such as isopropyl naphthaline sulfonate, and if need be an antioxidant such as hydroquinone sulfonate.

Initially, only alkaline developers were used. Thereafter, however, they tended to be replaced more and more by the neutral or weakly acid developers. The reason for this changeover is the sensitivity to oxidation of the most frequently used coupler, phloroglucinol, in the alkaline range, causing the developer solutions to be unstable and the developed papers to yellow very quickly. However, most conventional diazonium salts coupled with the above-mentioned couplers either too slowly or not at all in the neutral or weak-acid range, which is why new, very active-coupling diazonium compounds have had to be produced.

Various such photosensitive diazonium compounds have been described in the literature of the art, but only very few of them have proven to be usable in practice.

The most frequently used diazonium compounds in the technology of single-component diazotype material which is preferably developed neutrally or weakly acid are the stabilized 1-diazonium salts of 2,5-dialkoxy-4-thioarylbenzene and 2-amino-4-thioaryl-4-alkoxybenzene.

Single-component diazotype material which is sensitized with the first-mentioned diazonium compounds yields copies with black azo-dye formation when it is exposed image by image and developed with a weak-acid phloroglucinol developer. However, the azo dyes formed only slightly absorb the ultraviolet rays of the spectrum. This means that copies on transparent diazotype materials which are sensitized with the mentioned diazonium compounds are less suitable for use as so-called intermediate copies or subsidiary prints from which further copies can be made. Further drawbacks of 2,5-dialkoxy-4-thioarylbenzene diazonium salts are their moderate photosensitivity and rather slow development capacity.

The second group of diazonium compounds of the type consisting of 2-amino-4-thioaryl-5-alkoxybenzene diazonium salts, which are described in Swiss Pat. No. 448,734, corresponding to U.S. Pat. No. 3,311,475, represent a further development in the field of weakly-acid or neutrally coupling diazonium salts. The diazotype material sensitized with such diazonium salts has certain drawbacks, however. As compared with diazotype material sensitized with diazonium compounds of the first-mentioned group, this material is less suitable for storage. The storage capacity of the unexposed copying material is an important property of diazotype material, and it is a constant aim of diazo chemistry and diazo technology to improve this property.

Thus it is the object of the present invention to provide a diazotype material which presents improved properties as compared with prior art materials and which does not exhibit any of the aforementioned drawbacks.

To this end, the diazotype material according to the present invention contains a novel 2-substituent-3-thio-5-alkoxybenzene diazonium compound of the formula

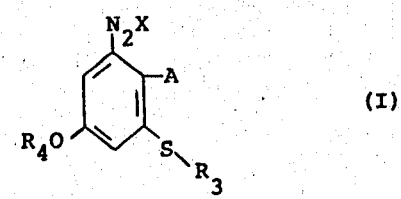

wherein
X is an anion,
A is the group

or —OR$_4$ in which
R$_1$ is hydrogen, an alkyl radical with 1–8 carbon atoms, a substituted phenyl, cycloalkyl, or aralkyl radical or a heterocyclic radical,
R$_2$ is an alkyl radical with 1–8 carbon atoms, a —COOR$_5$ group in which
R$_5$ signifies hydrogen, an alkyl radical with 1–8 carbon atoms, a cycloalkyl, aryl, aralkyl, or alkylaryl radical or a heterocyclic radical, or a group of

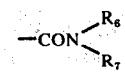

or —SO$_2$R$_6$ in which
R$_6$ and R$_7$ stand independently of one another for hydrogen or a hydroxy, alkoxy, alkyl with 1–4 carbon atoms, or phenyl radical,
R$_1$ and R$_2$ together with the nitrogen may be a morpholino, a methyl-substituted morpholino, pyrrolidino, or piperidino group, R₃ is an alkyl radical with 1–8 carbon atoms, an aralkyl, alkoxyaryl, haloaryl, alkoxyalkyl, or cycloalkyl radical or a heterocyclic radical, and R₄ is an alkyl, branched or unbranched lower alkyl, cycloalkyl, or aralkyl radical.

The diazonium compound defined above is advantageously produced for the diazotype material in the form of its salts such as chlorides, nitrates, oxalates, sulfates, and particularly in the form of its metal chloride double salts such as diazonium chloride-chlorozincate, -chlorostannate, -borofluoride, or the like, and preferably used in single-component diazotype material.

The novel diazonium compounds contained in the diazotype material according to the present invention exhibit unexpectedly essential advantages as compared with the known isomer compounds of U.S. Pat. No. 3,311,475.

The diazonium compound of formula I has been shown to have properties superior to those of the known diazonium compounds used in diazotype materials as regards storage capacity, solubility, and photosensitivity, for example.

The meta position of the thioaryl radical or of the thioalkyl radical with respect to the diazo group substantially increases the stability of the compounds, whereby the diazotype material sensitized with these diazonium salts exhibits very good storage capacity.

At the same time, these novel diazonium compounds have very good solubility, which, in turn, permits the more concentrated coating solution whereby a still greater actinic density of the material of the subsidiary prints is achieved. The use of these novel diazonium compounds is not limited merely to the production of single-component diazotype material to be developed with alkaline, neutral, or weakly-acid developers.

Although the recent German Disclosed Application No. 2,130,481 teaches diazonium compounds having a sulfur-containing group in meta position to the diazo group, these compounds differ from the compounds of formula I of the present invention particularly through the absence of a tertiary amino group in ortho position to the diazonium group. Moreover, the process of preparation is a substantially different one.

The novel photosensitive diazonium compounds can also be used in the so-called bicomponent diazotype material. This material differs from the single-component material described in that besides the stabilizing additives, both of the azo-dye-forming components, the diazonium salt and the coupler, are incorporated in the photosensitive layer of the copying material. After image by image exposure, such bicomponent material is developed with the aid of a gaseous medium, a liquid medium, or a medium causing an alkaline reaction in the presence of heat. This material neutralizes the acid stabilizing components of the photosensitive layer of the diazotype material, whereby the coupling reaction can be completed immediately. Because of the high coupling activity of the novel diazonium compounds, however, the choice of coupling components in bicomponent diazotype materials is limited to slow-coupling couplers. As examples of such couplers, β-resorcylic ethanolamide, 2-hydroxynaphthaline-3,6-disulfonic acid, and 7'-hydroxynaphtho-1',2',4,5-imidazole may be mentioned.

As an alkaline developer, ammonia vapor can be used in the so-called dry or ammonia process; optionally in the thermodiazo process, the agents causing an alkaline reaction in the presence of heat; or mixtures of lower organic amines with glycols in the so-called "pressure-diazo" or DP process.

Because of their high coupling activity, the novel diazonium compounds are preferably to be used for the sensitizing of single-component diazotype material. When developed with the usual weak-acid phloroglucinol developers, this diazotype material yields copies with dark red to brown, light-fast azodye images, while with weak-alkaline phloroglucinol developers, it yields copies with lighter colored, orange-red to brown, light-fast azo-dye images.

Particularly superior properties as described above are exhibited by that diazotype material according to the present invention which contains compounds of the formula Ia

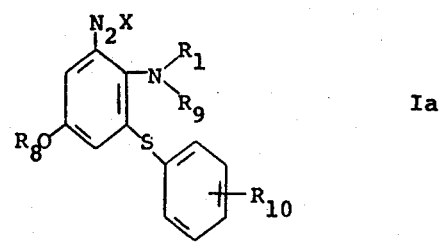

Ia wherein X is an anion, R₁ and R₈ independently of one another are methyl, ethyl, isopropyl, n-butyl, or β-methoxyethyl, R₉ is carboxymethyl, carboxyethyl, carboxyphenyl, or carboxyalkylphenyl, and R₁₀ is alkyl with 1–4 carbon atoms, halogen, alkoxy, or phenyl.

The novel diazonium compounds of formula I contained in the diazotype material according to the present invention may be produced by first nitrating and then halogenating, preferably brominating, a compound of formula II

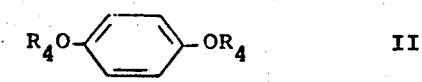

II whereupon a compound of formula III

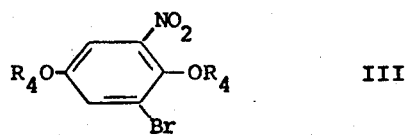

III is produced, reacting this compound with a thio compound of the formula HS-R₃ to the compound of formula IV

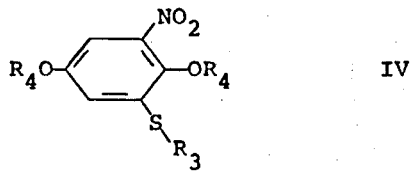

IV then reducing the 1-nitro-group and diazotizing the 1-amino compound obtained.

In the compound of formula IV, however, the 2-position —$OR_4$— group may also be treated with an amine $NH_2$—$R_1$ under pressure, the group —$NHR_1$ being introduced in the 2-position; this group may then be acylated. The above-mentioned reduction of the nitro group and diazotization may then follow this treatment.

By varying the process set forth above, e.g., by varying the pressure, the amount of intermediate components, the length of the reaction, or other working conditions, the desired compounds of formula I, preferably of formula Ia, may be obtained with an excellent yield. The single-component diazotype material sensitized with these diazonium salts, to be developed neutral-damp, can yield brown-violet to deep black color coatings.

The compound of formula Ia defined above, preferably contained in the diazotype material of the present invention, is advantageously obtained by first nitrating, then halogenating, preferably brominating, and treating the hydroquinone-dialkylether of the following formula IIa

IIa wherein $R_8$ signifies methyl, ethyl, isopropyl, n-butyl, or β-methoxyethyl, with p-thiocresol in an alkaline environment. Other substituted thiophenols and thionaphthols may also be used. The compound 2,5-dialkoxy-3-alkylphenylthio-nitrobenzene of formula IVa

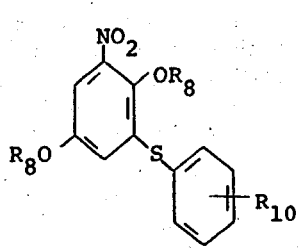
IVa wherein $R_8$ and $R_{10}$ are the above-mentioned substituents, is then reacted under pressure with aqueous or alcoholic methylamine or ethylamine, generally with alkylamine, at between 80° C. and 150° C. for from 1 to 20 hours, preferably at 120° C. for about 3 hours, whereupon the alkoxy group in the ortho position reacts to the nitro group. The reaction product 2-alkylamine-3-alkylphenylthio-5-alkoxy-nitrobenzene is reacted with acylation agents such as acetic anhydride or benzoyl chloride, or with chlorine-active compounds such as benzyl chloride, chloracetic acid, chloracetic ethylester, chloroformic ethylester, chloroformic methylester, or chloroformic benzylester in the presence of alkaline or alkaline earth compounds, preferably of magnesium oxide, and other acid-neutralizing metal oxides, hydroxides, or carbonates. The 2-N-alkoxycarbonyl-N-alkylamino-3-alkylphenylthio-5-alkoxynitrobenzene obtained is catalytically reduced, the amine compound diazotized in the usual manner, and the end product Ia isolated as diazonium chloride-zinc chloride double salt.

As explained above, the use in diazotype materials of the novel diazonium compounds of formula I, especially of the preferably produced compounds of formula Ia, presents numerous superior advantages, likewise described above.

EXAMPLE 1

A cellulose acetate layer of about 20 g/m², applied to natural transparent paper of approximately 75 g/m², is superficially hydrolyzed to a depth of about 4 microns; after the removal of the alkaline-reacting chemicals used for the hydrolysis, it is washed with water and sensitized with a solution of the following composition:

5 g  2-N-ethoxycarbonyl-N-methylamino-3-(4'-methyl)-phenylthio-5-methoxy-benzene diazonium chloride-zinc chloride double salt (see formula 5 below and according to the process described below)

0,2 g boric acid
0,5 g tartaric acid
35 ml ethanol (95%)
65 ml water (desalinized).

The excess of the solution applied is removed, and the paper is dried.

A sheet of the diazotype subsidiary print material thus coated is exposed image by image and developed with a weakacid developer "N". The developer "N" is a solution of 6 g phloroglucinol
4 g resorcinol
140 g sodium formate
14 g sodium benzoate
1 g 2-ethylhexanol sodium sulfonate in 1000 ml of water.

The developed subsidiary print shows a dark brown-violet azo-dye image with high ultraviolet absorption.

The development capacity of this diazotype material is excellent. The undeveloped material was subjected to the accelerated aging test. The test conditions were: relative humidity of 50% ± 2% and temperature of 50° C. ±1°. After each 24-hour period, a piece is cut off the sheets subjected to aging, exposed through a test pattern, and developed with developer "N". The diazotype material coated with novel diazonium salt according to the present invention remains undiscolored for a long time and retains the high actinic density of the color coating. On copies subsequently produced on opaque diazotype material, the covering power and the transparency of the diazotype material thus stored, which was used as a test pattern, could be precisely evaluated.

EXAMPLE 2

A cellulose acetate film was coated with a solution of the following composition, the excess was removed, and the film was dried:

50 ml desalinized water
30 ml isopropyl alcohol
10 ml n-butyl alcohol
5 ml formic acid
6 g sulfosalicyclic acid
2 g thiourea
1,5g β-resorcylic ethanolamide
3,5g  2-N-ethoxycarbonyl-N-methylamino-3-(4'-methyl)-phenylthio-5-methoxy-benzene diazonium chloride-chlorozincate (according to the manner set forth below).

The diazotype paper thus coated is exposed image by image and developed in ammonia vapor. The developed subsidiary print shows an intense purple azo-dye image on a clear and undiscolored background.

The compound contained in the diazotype material in Examples 1 and 2, viz., 2-N-ethoxycarbonyl-N-methylamino-3-(4'-methyl)-phenylthio-5-methoxy-benzene diazonium chloride-chlorozincate of formula 5

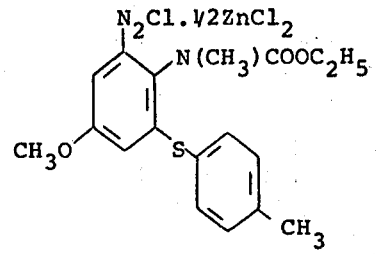

can be produced as follows: The stated melting-points of the compounds are corrected. The $R_f$ values relate to a thin-layer chromatogram--silicagel DC finished plates (Merck No. 5724)— using toluol as the flow agent. The infrared spectra were taken in potassium bromide. Parts given are parts by weight, and their ratio to parts by volume is as g to ml.

Dimethylhydroquinone is nitrated in glacial acetic acid with 30% nitric acid, and the 2,5-dimethoxy-nitrobenzene is brominated in carbon tetrachloride using a metal catalyst at 40°C. The solution is washed neutral with large amounts of water, evaporated in vacuo, and the residue dissolved in hot methanol. The 2,5-dimethoxy-3-bromo-nitrobenzene crystallizes out as a light yellow product.

Melting-point = 112° C., $R_f$ = 0.70.

Two parts of the resultant 2,5-dimethoxy-3-bromonitrobenzene are treated with one part thiocresol, one part sodium carbonate, in 22 parts of a solvent mixture of ethanol-water 1:1. The reaction mixture is allowed to react for 8 hours at 60°C.; the suspension is filtered warm, the residue is washed free of thiocresol with diluted soda lye and then washed neutral with large amounts of water. The raw material is recrystallized out of ethanol. The result is 1.4 parts yellow crystals of 2,5-dimethoxy-3-(4'-methyl)-phenylthio-nitrobenzene with a melting-point of 119°–120° C., $R_f$ = 0.72.

Infrared spectrum in KBr

| | |
|---|---|
| 730, 830, 1075, 1155 | $cm^{-1}$ = 1,3,5-substituted phenyl |
| 1315, 1505 | $cm^{-1}$ = aryl-NO$_2$ |
| 2840 | $cm^{-1}$ = —OCH$_3$ |
| 2920 | $cm^{-1}$ = —CH$_3$ |
| 3020 | $cm^{-1}$ = =CH(aryl) |

One part 2,5-dimethoxy-3-(4'-methyl)-phenylthio-nitrobenzene is allowed to react with 0.5 parts aqueous methylamine in two parts dioxane under pressure at between 100° and 120° C., according to the purity of the dimethoxy compound, for three hours; the solution is evaporated dry, the residue absorbed in methanol, and the precipitate filtered. The raw material is recrystallized out of ethanol dioxane 2:1. The result is 0.6 to 0.8 parts redish orange crystals of 2-methylamino-3-(4'-methyl)-phenylthio-5-methoxy-nitrobenzene.

Melting-point: 153°C.; $R_f$ = 0.48.

2-N-ethoxycarbonyl-N-methylamino-3-(4'-methyl)-phenylthio-5-methoxy-nitrobenzene is prepared as follows: one part of the above-obtained 2-methylamino-3-(4'-methyl)-phenylthio-5-methoxy-nitrobenzene is allowed to react with one part chloroformic ethylester and 0.4 parts magnesium oxide in eight parts benzene at 70° C. with stirring for 16 hours. The reaction mixture is filtered warm, the solution evaporated, and the residue dissolved in 3.5 parts ethanol. After cooling of the solution, 1.1 parts yellow, photosensitive crystals are precipitated out, with F = 115° C., $R_f$ = 0.46.

2-N-ethoxycarbonyl-N-methylamino-3-(4'-methyl)-phenylthio-5-methoxy-aniline is prepared from the above nitro compound by catalytic hydrogenation using Raney nickel in dioxane at room temperature with quantitative yield as white needles which melt at 142° C.

One part 2-N-ethoxycarbonyl-N-methylamino-3-(4'-methyl)-phenylthio-5-methoxy-aniline is suspended in eight parts ice water with the addition of non-ionogenic emulsifier, one part by volume of concentrated hydrochlorid acid is added, and the white suspension is diazotized at between 3° and 5° C. with 1.2 parts 25% sodium nitrite solution. The suspension dissolves with a yellow coloring. A cold solution of one-half part zinc chloride, one-half part concentrated hydrochloric acid, and one part water is added to the diazo solution by drops with vigorous stirring, and the yellow precipitate is then suction-filtered. The product is dissolved in 40 parts warm water, the solution is filtered warm and poured into a solution of zinc chloride and water, acidified with hydrochloric acid, with stirring and cooling. The product, which coagulates in yellow flakes, is suction-filtered, the suction-filrate is pressed almost dry with a hand-press and dried in vacuo over calcium chloride. It yields 1.2 parts greenish yellow product with a melting-point of 141° to 142° C. with simultaneous decomposition.

| Analysis | Calculated | Found |
|---|---|---|
| C | 46.79% | 46.6% |
| H | 4.36% | 4.5% |
| N | 9.09% | 9.0% |
| Total Cl | 15.35% | 15.3% |
| Zn | 7.07% | 7.0% |
| Water | — | 1.6% |

If, with reference to the following Table 1, the starting 1,4-dimethoxybenzene is replaced by 1,4-dialkoxy-benzene from column 2, and the chloroformic ethylester is replaced by the compounds from column 3, in the same proportions as given above and working otherwise in the same manner, the products Nos. 6–9, with the decomposition points mentioned in column 5, are obtained.

Column 1 contains the formula number of the corresponding diazonium compound.

Table 1

| 1 | 2 | 3 | 4 | 5 |
|---|---|---|---|---|
| 6 | C₂H₅O—⟨⟩—OC₂H₅ | ClCOOC₂H₅ | (structure with N₂Cl·½ZnCl₂, N(CH₃)COOC₂H₅, C₂H₅O, S-C₆H₄-CH₃) | 135 |
| 7 | n—C₄H₉O—⟨⟩—O—nC₄H₉ | ClCOOC₂H₅ | (structure with N₂Cl·½ZnCl₂, N(CH₃)COOC₂H₅, n—C₄H₉O, S-C₆H₄-CH₃) | 146 |
| 8 | C₂H₅O—⟨⟩—OC₂H₅ | ClCOOCH₃ | (structure with N₂Cl·½ZnCl₂, N(CH₃)COOCH₃, C₂H₅O, S-C₆H₄-CH₃) | 131 |
| 9 | CH₃O—⟨⟩—OCH₃ | ClCOOCH₂—⟨⟩ | (structure with N₂Cl·½ZnCl₂, N(CH₃)COOCH₂—⟨⟩, CH₃O, S-C₆H₄-CH₃) | 128 |

These compounds of formulae 6 to 9, too, showed the superior advantages in diazotype materials of the compound of formula 5 utilized in Examples 1 and 2.

EXAMPLE 3

A cellulose acetate layer of about 20 g/m², applied to natural transparent paper of approximately 75 g/m², is superficially hydrolyzed to a depth of about 4 microns. After the removal of the alkaline-reacting chemicals used for the hydrolysis, it is washed with water and sensitized with a solution of the following composition:
70 ml desalinized water
30 ml ethanol (95%)
1,5 g 2,7-naphthaline disulfonate
6 g sulfosalicylic acid
1,5 g β-resorcylic ethanolamide
3,5 g 2,5 -dimethoxy-3-(4'-methyl)-phenylthiobenzene diazonium chloride-zinc chloride double salt (formula 10).

After scraping off of the excess and drying, the diazotype material is exposed image by image and developed in a pressure-diazo machine (Admel Ltd., Weybridge, England) with the aid of a DP activator. According to British Pat. No. 1,143,702 (Addressograph-Multigraph, U.S.A.), such an activator consists, for example, of 60% monoethanolamine, 20% hexylene glycol, and 20% water. The developed subsidiary print shows a light orangebrown azo-dye image with high actinic density.

The above-mentioned diazonium salt of formula 10

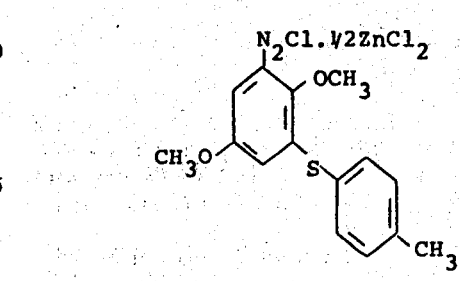

10 can be prepared as follows:

Starting with dimethylhydroquinone, it is first nitrated and then brominated, in the manner described in Example 2, and the resultant 2,3-dimethoxy-3-bromonitrobenzene is reacted with thiocresol. The resultant 2,5-dimethoxy-3-(4'-methyl)-phenylthionitrobenzene is converted quantitatively into 2,5-dimethoxy-3-(4'-methyl)-phenylthioaniline by catalytic hydrogenation using Raney nickel as catalyst in dioxane at room temperature. This product crystallizes in the form of white needles which melt at 155°C.

One part of the 2,5-dimethoxy-3-(4'-methyl)-phenyl-thioaniline is suspended in 10 parts ice water with the addition of an emulsifier, 1.5 parts by volume of concentrated hydrochloric acid are poured in, and the light violet suspension is diazotized with 1.25 parts 25% sodium nitrite solution at a temperature of from 3° to 5° C. The suspension dissolves with a greenish yellow coloring. There follows the addition by drops of 2.5 parts of a 25% zinc chloride solution which has been acidified with hydrochloric acid. The addition takes place with vigorous stirring. The brown precipitate formed is suction-filtered, then dissolved in 30 parts warm water, the solution is filtered warm and poured into a hydrochloric zinc chloride solution with stirring and cooling. The product, which coagulates in yellowish brown flakes, is suction-filtered and largely freed of liquid with the aid of a hand-press. Drying in vacuo over calcium chloride follows. Yield: 0.9 parts of the diazonium-zinc chloride double salt which has a melting-point of 152°C. with simultaneous decomposition.

| Analysis | Calculated | Found |
|---|---|---|
| C | 46.08% | 46.2% |
| H | 3.87% | 3.9% |
| N | 7.17% | 7.3% |
| S | 8.20% | 8.3% |
| Total Cl | 18.14% | 17.8% |
| Ionogenic Cl | 18.14% | 17.8% |
| H₂O | — | 0.96% |
| Zn | 8.36% | 8.3% |

EXAMPLE 4

White paper of 80 g/m² is sensitized with liquid of the following composition:
2 g 2,5-dimethoxy-3-(4'-methyl)-phenylthiobenzene diazonium chloride-zinc chloride double salt
0,5 g citric acid
0,8 g aluminum sulfate
3,5 ml aqueous polyvinylacetate dispersion (55%7
100 ml desalinized water The excess liquid is removed as usual, and the material is then dried. This photosensitive copying paper is exposed image by image and developed with a weakly acid developer "N". The developed copy shows a black azo-dye image which stands out in sharp contrast to the white paper background.

The method of preparation of the diazonium salt is described in Example 3, and the composition of the developer has been mentioned in Example 1.

What is claimed is:

1. A diazotype composition containing a 2-substituent-3-thio-5-alkoxybenzene diazonium compound of the formula:

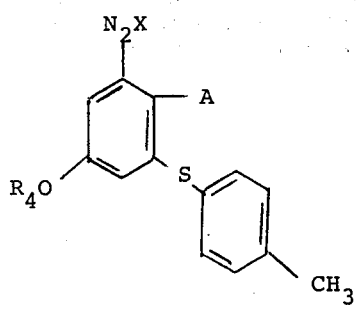

wherein
A is $-OR_4$ or $-N(CH_3)COOR_5$;
$R_4$ is a lower alkyl radical and
$R_5$ is an alkyl radical having 1–8 carbon atoms, or a benzyl radical and
X is an anion.

2. A diazotype composition according to claim 1 containing a diazonium compound of the formula

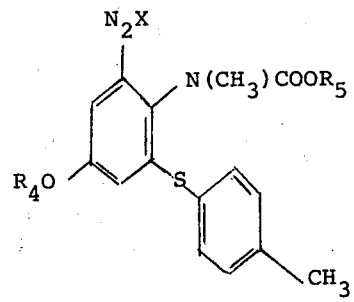

wherein $R_4$, $R_5$, and X are as defined in claim 12.

3. A diazotype composition according to claim 1 containing a diazonium compound of the formula

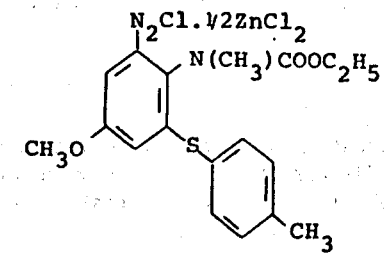

4. A diazotype composition according to claim 1 containing a diazonium compound of the formula

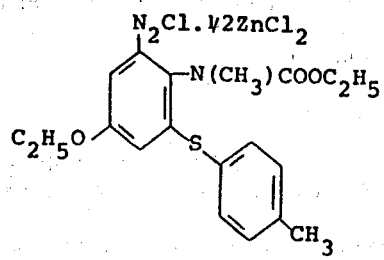

5. A diazotype composition according to claim 1 containing a diazonium compound of the formula

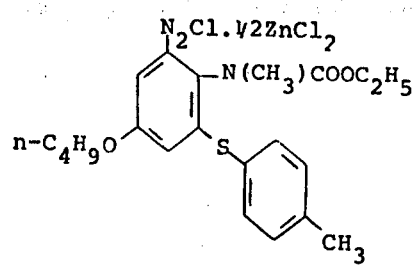

6. A diazotype composition according to claim 1 containing a diazonium compound of the formula
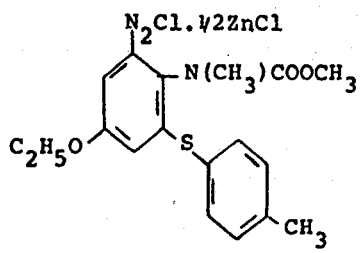
7. A diazotype composition according to claim 1 containing a diazonium compound of the formula
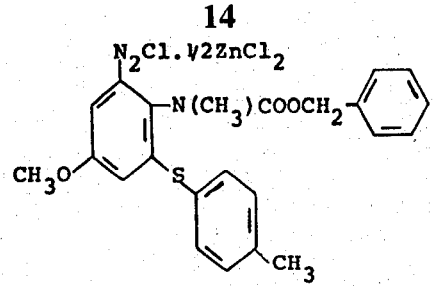
8. A diazotype composition according to claim 1 containing a diazonium compound of the formula
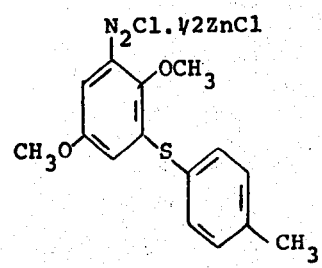
* * * * *